United States Patent
Cantor

(10) Patent No.: US 6,921,844 B2
(45) Date of Patent: Jul. 26, 2005

(54) METHOD FOR FORMING A SCENTED ADHESIVE BANDAGE

(76) Inventor: Joy L. Cantor, 6629 Chelsea Bridge, West Bloomfield, MI (US) 48322

(*) Notice: Subject to any disclaimer, the term of this patent is extended or adjusted under 35 U.S.C. 154(b) by 0 days.

(21) Appl. No.: 10/935,374

(22) Filed: Sep. 7, 2004

(65) Prior Publication Data

US 2005/0033214 A1 Feb. 10, 2005

Related U.S. Application Data

(63) Continuation of application No. 09/689,194, filed on Oct. 12, 2000, now Pat. No. 6,787,679.

(51) Int. Cl.$^7$ ................................................ A61F 13/00
(52) U.S. Cl. ........................... 602/41; 602/42; 602/52; 602/55; 602/57
(58) Field of Search ............ 602/41–59; 424/443–449; 604/304–308; 206/440, 441; D24/189

(56) References Cited

U.S. PATENT DOCUMENTS

| | | |
|---|---|---|
| 3,830,237 A | 8/1974 | Bernardin et al. |
| 4,254,179 A | 3/1981 | Carson, III et al. |
| 4,285,338 A | 8/1981 | Lemelson |
| 4,334,530 A | 6/1982 | Hassell |
| 4,549,653 A | 10/1985 | Lauritzen |
| 4,826,497 A | 5/1989 | Marcus et al. |
| 4,880,690 A | 11/1989 | Szycher et al. |
| 4,917,920 A | 4/1990 | Ono et al. |
| 5,071,704 A | 12/1991 | Fischel-Ghodsian |
| 5,156,843 A | 10/1992 | Leong et al. |
| 5,534,105 A | 7/1996 | Boyd |
| 5,577,947 A | 11/1996 | Malloy et al. |
| 5,591,146 A | 1/1997 | Hasse |
| 5,618,457 A | 4/1997 | Wilkinson |
| 5,714,445 A | 2/1998 | Trinh et al. |
| 5,769,832 A | 6/1998 | Hasse |
| 5,769,833 A | 6/1998 | Hasse |
| 5,776,378 A | 7/1998 | Knight |
| 5,817,835 A | 10/1998 | Krishnamurti et al. |
| 5,970,300 A | 10/1999 | Acquaviva |

FOREIGN PATENT DOCUMENTS

WO     WO 93/09818     5/1993

Primary Examiner—Kim M. Lewis
(74) Attorney, Agent, or Firm—Brooks Kushman P.C.

(57) ABSTRACT

An adhesive bandage is provided an is adapted to be applied to a user's skin wound. The bandage includes a flexible backing layer having a rear surface, a pad portion attached to the rear surface of the backing layer, an adhesive portion disposed on the rear surface of the backing layer away from the central pad portion. The adhesive is used to adhere the bandage to the user's skin. Also included are fragrance portions disposed within the adhesive portion and a release cover releasably secured to the adhesive portion, which when removed, allows for release of a scent associated with the fragrance portions. Also, characters may be included on the bandages which correspond to the scent released.

9 Claims, 2 Drawing Sheets

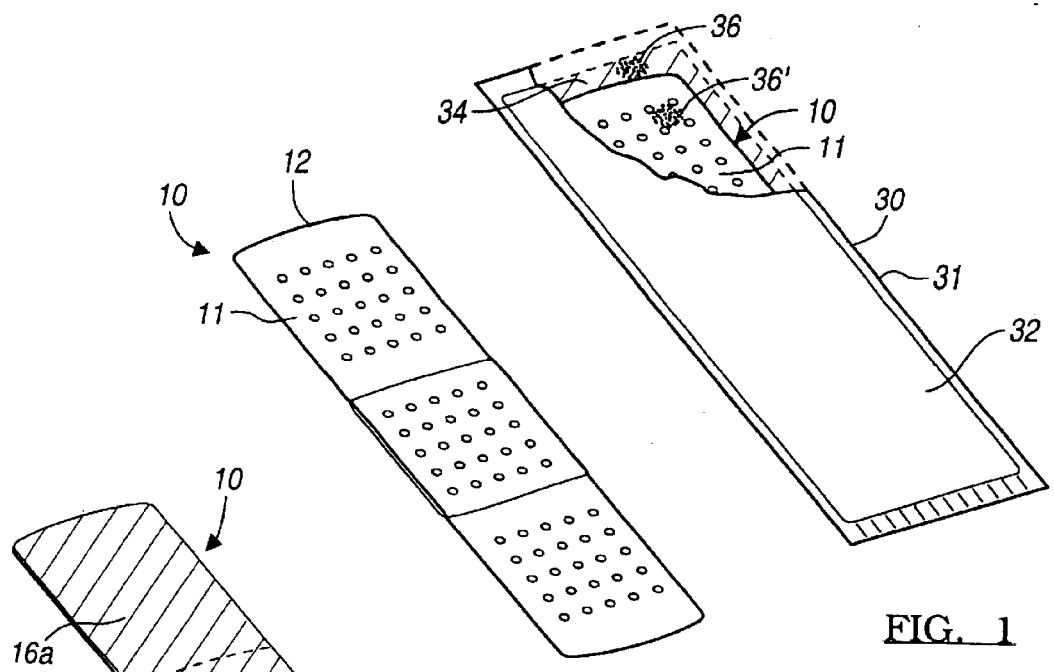
FIG. 1
FIG. 2
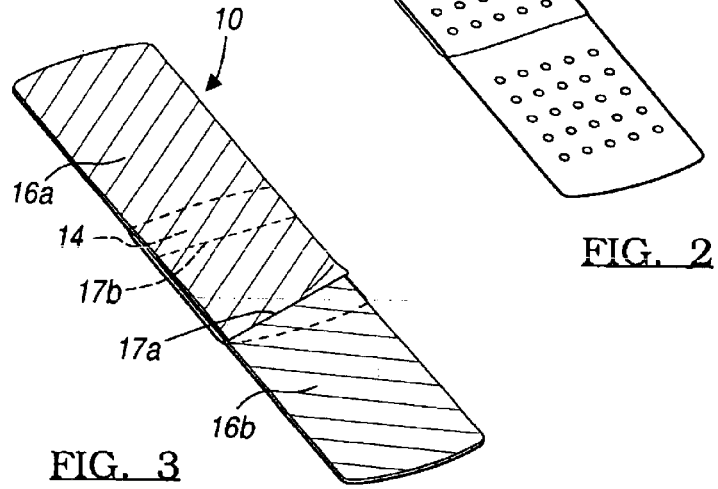
FIG. 3
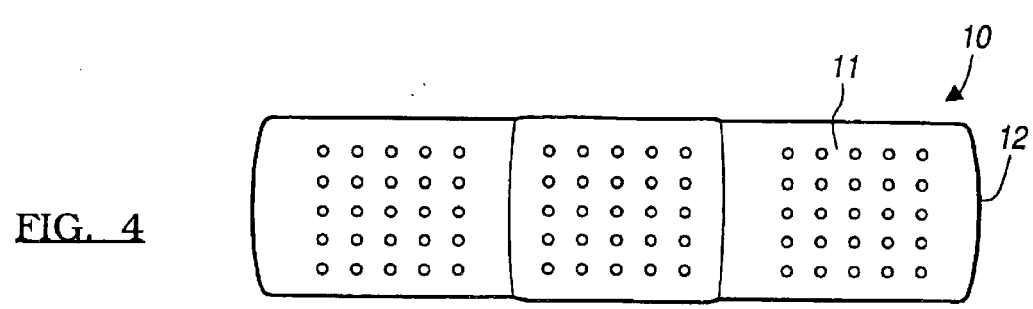
FIG. 4
FIG. 5

METHOD FOR FORMING A SCENTED ADHESIVE BANDAGE

This is a continuation of application Ser. No. 09/689,194,, filed Oct. 12, 2000, now U.S. Pat. No. 6,787,679.

TECHNICAL FIELD

The present invention relates to a scented adhesive bandage.

BACKGROUND ART

Adhesive bandages are a popular and widely used form of dressing to protect relatively small or minor skin wounds and blemishes. When used on children, the application of an adhesive bandage, by itself, may not be enough to overcome the child's initial reaction upon receiving the wound. As many parents can attest, a child who accidentally falls and scrapes a knee or elbow may provide a reaction that results from 5% physical pain and 95% emotional factors, such as surprise, fear, abandonment, etc. (these numbers have not scientifically researched by inventor but instead come from practical experience).

Currently, there exists in the marketplace adhesive bandages directed particularly for use with children. These bandages have screened-on designs which are appealing to children, and include, for example, animal shapes, cartoon or other fictional characters, or bold colors. Such designs are marketed to help "overcome" the aforementioned emotional reactions of children by directing their attention away from the wound and toward something visually appealing.

However, the visual stimulation of the bandage design is often not enough to calm the child. Accordingly, there is a need for an adhesive bandage which helps to calm a child and overcome the emotional reaction caused by a minor skin wound or blemish to which an adhesive bandage would be applied under normal circumstances. Such an improved adhesive bandage should be relatively easy to manufacture and use.

DISCLOSURE OF INVENTION

It is a principal object according to the present invention to provide an improved adhesive bandage which is able to improve a child's mood or emotional discomfort upon receiving a minor flesh wound, or other skin condition to which an adhesive bandage would be applied under normal circumstances.

It is another object according to the present invention to provide an adhesive bandage which provides for sensory stimulation to a child or other user who has a minor wound to which the adhesive bandage is suitably applied.

It is still another object according to the present invention to provide an adhesive bandage which provides olfactory stimulation to a child or other user to whom the bandage is applied.

It is yet another object according to the present invention to provide an adhesive bandage having olfactory, visual and auricular stimulation to a person to whom the bandage is applied.

Accordingly, keeping with the goals and objectives according to the present invention, a first embodiment provides for an adhesive bandage which is adapted to be applied to a user's skin wound. The adhesive bandage includes a flexible backing layer having a rear surface, a pad portion which is attached to the rear surface of the backing layer, and an adhesive portion which is disposed on the rear surface of the backing layer away from the central pad portion. The adhesive adheres the bandage to the user's skin. Also included are fragrance portions which are disposed within the adhesive portion, and a release cover which is releasably secured to the adhesive portion, which when removed, allows for release of a scent associated with the fragrance portions. In this embodiment, the adhesive bandage the fragrance portions include micro-capsules of fragrance. Also, the release cover sheers the fragrance portions when removed in order to release the scent.

In another embodiment, an adhesive bandage and wrapper assembly is provided which includes a sealed wrapper which has an inner surface and an interior compartment. It also includes an adhesive bandage which is disposed within the interior compartment of the sealed wrapper and which has an adhesive side and a non-adhesive side. Also included is a fragrance portion disposed on at least one of the inner surface of the sealed wrapper and non-adhesive side of the adhesive bandage, such that the when the sealed wrapper is opened, a scent is released which is associated with the fragrance portion.

Any of the adhesive bandages disclosed herein may include at least one character disposed thereon which corresponds to the scent released.

Also provided in accordance with the teachings disclosed herein, a method of forming a wrapped and scented adhesive bandage includes providing a wrapper having an inner surface and an outer surface; applying a fragrance having a scent to the inner surface of the wrapper or the outer surface of the bandage; positioning an adhesive bandage proximate the inner surface of the wrapper; and sealing the wrapper so that it encloses the adhesive bandage and the scent of the fragrance. It is contemplated that applying the fragrance includes applying a scented liquid or spray to the inner surface of the wrapper or the exterior surface of the bandage.

The above objects and other objects, features, and advantages of the present invention are readily apparent from the following detailed description of the best modes for carrying out the invention when taken in connection with the accompanying drawings.

BRIEF DESCRIPTION OF DRAWINGS

FIG. 1 is a perspective view illustrating an adhesive bandage in a wrapper according to one embodiment of the present invention.

FIG. 2 is a perspective view of the outer surface of the bandage according to the present invention;

FIG. 3 is a perspective view of the bandage showing the release liner portions according to the present invention;

FIG. 4 is a top plan view of the bandage of FIG. 2; and

FIG. 5 is side elevational view of the bandage according to the present invention, prior to having the release liner assembled thereon;

BEST MODE FOR CARRYING OUT THE INVENTION

Figure 6:
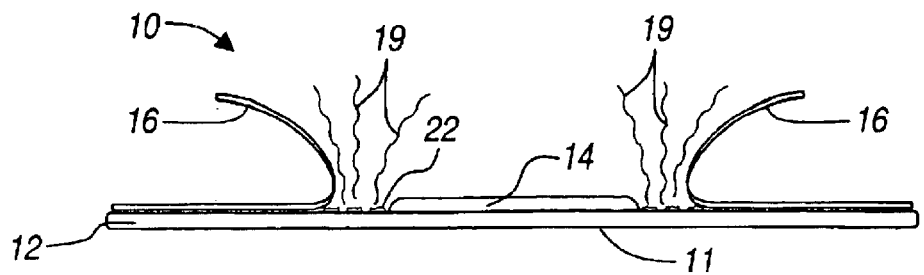
FIG. 6 is a side elevational view of the bandage according to the present invention with the release liner in the process of being removed.

FIG. 1 is a perspective view illustrating the inner surface of an adhesive bandage 10 in a wrapper 30 according to the present invention. In keeping with the teachings according to the present invention, the bandage 10 is accompanied by a scent or fragrance during use.

With reference to FIG. 1, bandage 10 is removed from a sealed wrapper 30 or sheath prior to use. Wrapper 30 has a sealed edge 31, an outer surface 32, and an inner surface 34 which when sealed defines an inner compartment. In a first embodiment according to the present invention, the inner surface 34 of wrapper 30 has a fragrance 36 or scent applied thereon, the bandage 10 is inserted into the wrapper 11, and the wrapper 11 is sealed, thereby enclosing and enveloping the bandage, such that the fragrance cannot escape. It is contemplated that the fragrance portion 36 is applied by spraying or misting a liquid fragrance thereon. The wrapped bandage is then ready to be opened and used by the end-user. Accordingly, when the wrapper 30 is opened by the end-user, the scent associated with the fragrance 36 is emitted and accompanies the bandage 10, which can then be smelled by the user. The outer surface of the bandage 10 may also have residue of the fragrance disposed thereon as a result of being inside wrapper 30 and proximate to inner surface 34. Such smell may particularly put an upset child at ease and lessen or offset the severity of the wounded child's emotional reaction.

In another embodiment, also illustrated in FIG. 1, the fragrance 36' may also be sprayed or otherwise applied to the outer surface (or front surface or non-adhesive side) of the bandage 10. The bandage is then sealed within a wrapper 31, thereby containing the scent within wrapper 31, as described above. Thus, when the wrapper is opened, the scent is released. Of course, the fragrance portion is preferably biocompatible and should not react with or cause irritation with the user's skin. However, because the fragrance portion is either applied directly to the wrapper or to the non-adhesive side of the bandage, it reduces any possibility that the fragrance could contact and cause irritation to the skin.

Another embodiment according to the present invention is also disclosed herein. In this embodiment, the fragrance and scent feature of bandage 10 is independent of wrapper 11. Specifically, FIG. 2 illustrates a perspective view of the outer surface 30 of the bandage 10, FIG. 3 illustrates a perspective view of the rear surface of bandage 10, and FIG. 4 illustrates a top plan view of bandage 10. FIG. 5 shows a side elevational view of bandage 10 prior to a release liner 16 (or cover) being applied thereon, and FIG. 6 illustrates a side elevational view of bandage 10 showing release liner 16 partially removed by the user. As illustrated therein, bandage 10 includes a flexible base portion 12, which as known to those skilled in the art may be formed of a plastic or fabric material for adjusting to the shape of the body portion to which the bandage 10 is applied, as well as for accommodating active movement of the wounded body portion, such as a knee or a knuckle.

With further reference to FIG. 1, bandage 10 also includes a centrally disposed pad or gauze material 14 which covers and protects the wound when the bandage 10 is in use, without adhering to the wound. The inner surface 15 of bandage 10 includes an adhesive portion 18 on each side of pad member 14.

Prior to use, base material 12 has attached to its inner surface one or more liner portions 16 (or pull strip) which cover the inner surface 15 of bandage 10 in order to keep pad member 14 clean and sterile and also keep the adhesive portion 18 fresh. The adhesive portion 18 allows bandage 10 to adhere to the user's body parts surrounding the wound. The liner layer 16 is applied to the polyurethane membrane 12 to cover pressure sensitive adhesive 18. The release liner 16 is applied to the rear surface on which the adhesive 18 is found.

In use, the release liner 16 is pulled from the rear surface 15 of the bandage 10, thereby uncovering the pad portion 14 and the adhesive portions 18. In keeping with the teachings according to the present invention, removing the release liner 16 from the adhesive portions 18 also releases the scent according to the present invention. Particularly, in one embodiment, micro-capsules 22 of a predetermined scent are embedded in adhesive portion 18 as illustrated in FIG. 5. Release liner 16 is then applied on top of the adhesive 18 (with micro-capsules 22) without rupturing them. As illustrated in FIG. 6, when release liner 16 is removed from the adhesive portion 18 and peeled back, the sheer force across the tops of micro-capsules 22 causes them to break and release the scent 19. This and other ways to release such scent is more particularly described in U.S. Pat. No. 5,769,832, which is incorporated herein by reference. The scent preferably is one that appeals to young children and is distinctive. Such scent may include, but is not limited to, smells of fruit (such as strawberry, grape or watermelon), bubble gum, root beer, candy, or may even include a more familiar scent, such as a perfume worn by a grandmother, apple pie, or flowers, or a variety of other childrens' favorites, such as buttered popcorn, chocolate, or peanut butter.

Accordingly, the familiar smell released from the bandage works to calm or relax a child more than the visual graphics of current adhesive bandages, particularly if the child is crying, and is not able to focus on the design of the bandage. It is contemplated, of course, that in order to sheer the micro-capsules and release the scent, that the pull strength needed to release the protective covering from the adhesive portion is relatively greater than the present design which is removed in a relatively smooth and easy manner.

The present invention contemplates that a scent may be a burst of fragrance or a relatively slow release diffusion of scent. It is also fully contemplated that in order to achieve the desired goals and objectives, the scent may be applied to only a small portion of the adhesive. Further, the scent may also be kept relatively distal from the pad portion 14 such that the scent is not close enough to the wound to cause irritation.

Preferably, the scent producing chemicals and the adhesive do not plasticize or cause the adhesive to loose its adherence or otherwise react with the adhesive to leave residue on the user's skin. Accordingly, the chemicals must be biocompatible for contact with the skin.

Another method of applying the scent to the adhesive bandage is disclosed in U.S. Pat. No. 4,880,690, which is incorporated herein by reference, or U.S. Pat. No. 5,071,704, or any of the other ways known to those skilled in the art.

As noted above, the micro-capsule containing adhesive 18 is attached directly to the rear surface 15 of backing member 12. Pull strip 16 is laid directly over binder and is attached thereto. Pull strip 16 will preferably fully cover the binder. As shown in FIG. 3, pull strip 16 fully covers binder and has two portions 16a and 16b which overlap and having inner edges 17a and 17b, respectively, that extend over pad member 14 in order to provide protection for it. The pull strip is preferably formed of polyethylene, polypropylene, or other materials known in the art.

Figure 7A:
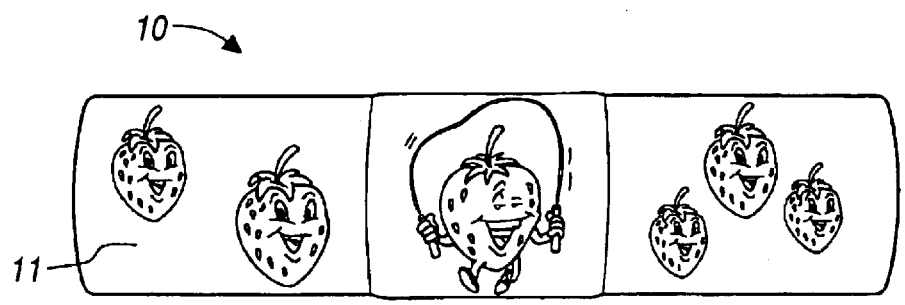
FIGS. 7a, 7b, and 7c illustrate an outer surface of the bandage according to the present invention, showing representative characters having names and designated personalities according to the present invention.
Figure 7B:
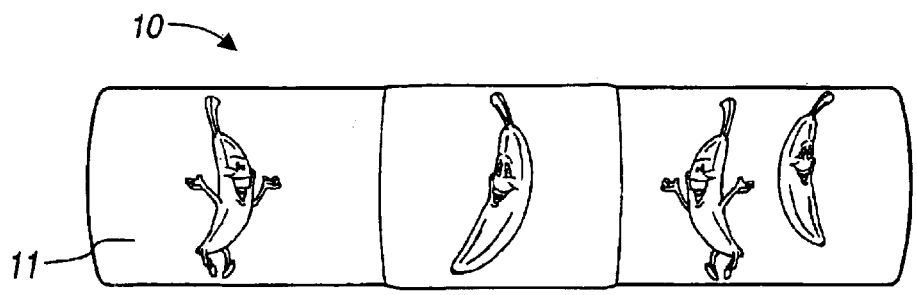
Figure 7C:
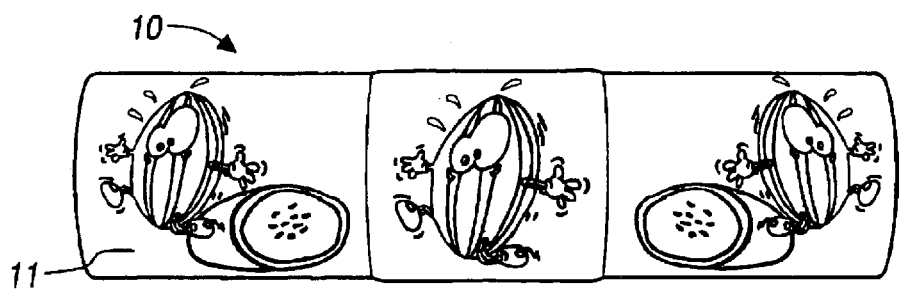

In addition to the scent feature, it is contemplated that the outer surface 11 of bandage 10 can also include characters or illustrations to accompany the scents. For example, as illustrated in the bandages of FIGS. 7a, 7b, and 7c, the characters are screened (or are otherwise positioned) onto the bandages 10 and each character can also have a fanciful name, such as "Silly Sam, The Smiling Strawberry" (see design of FIG. 7a), "Banana Bob Being Bashful" (see design of FIG. 7b), or "Wacky Watermelon Willy" (see design of FIG. 7c), to accompany, respectively, a strawberry, banana or watermelon scented bandage 10. Such alliterative names and descriptions may also serve to promote teaching and sound recognition among younger children, as well as teaching an association between a scent, its name, and the identification of the object that produces such scent. Thus, each character could have its own personality characteristic, such as lopsided eyes, big toothy grin, lots of freckles, etc. Accordingly, under the proper circumstances, the character and name features, in association with the scent, serve to offset and lessen a child's sometimes over-reaction to a small scrape or wound. The scents, characters, and names could also be used to play educational games, such as matching the fruit scented bandages.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of forming an adhesive bandage configured to be applied to a user's skin wound, the method comprising:

providing a flexible backing layer having a front surface and a rear surface;

providing a pad portion attached to the rear surface of the backing layer;

providing an adhesive portion disposed on the rear surface of the backing layer away from a central area of the pad portion for adhering the bandage to the user's skin;

applying fragrance portions to the adhesive portion; and sealing the adhesive portions with a release cover, which when removed, allows for release of a scent associated with the fragrance portions.

2. The method of claim 1 wherein applying the fragrance portions includes embedding micro capsules of fragrance into the adhesive portion.

3. The method of claim 1 wherein applying the fragrance portions includes spraying fragrance portions onto the adhesive portion.

4. The method of claim 1 further comprising providing a pair of adhesive portions on the rear surface of the backing layer on opposing sides of the pad portion.

5. The method of claim 1 further comprising applying a character to the front surface of the flexible backing layer which corresponds to the scent released.

6. A method of forming a wrapped and scented adhesive bandage, the method comprising:

providing a wrapper having an inner surface and an outer surface;

providing an adhesive bandage to be applied to a user's skin wound including a flexible backing layer having a front surface and a rear surface, a pad portion attached to the rear surface of the backing layer and an adhesive portion disposed on the rear surface of the backing layer away from a central area of the pad portion for adhering the bandage to the user's skin;

applying a fragrance having a scent to the front surface of the bandage;

positioning the adhesive bandage proximate the inner surface of the wrapper; and sealing the wrapper so that it encloses the adhesive bandage and the scent of the fragrance.

7. The method of claim 6, wherein applying the fragrance includes applying a scented liquid to the front surface of the bandage.

8. The method of claim 6, wherein providing the wrapper includes a wrapper having a character therein corresponding to the scent of the fragrance.

9. The method of claim 6 further comprising applying a character to the front surface of the flexible backing layer which corresponds to the scent of the fragrance.

* * * * *